(12) United States Patent
Sommargren

(10) Patent No.: US 6,177,993 B1
(45) Date of Patent: Jan. 23, 2001

(54) INSPECTION OF LITHOGRAPHIC MASK BLANKS FOR DEFECTS

(75) Inventor: Gary E. Sommargren, Santa Cruz, CA (US)

(73) Assignee: The Regents of the University of California, Oakland, CA (US)

(*) Notice: Under 35 U.S.C. 154(b), the term of this patent shall be extended for 0 days.

(21) Appl. No.: 09/455,853

(22) Filed: Dec. 7, 1999

(51) Int. Cl.[7] .................................................. G01N 21/00
(52) U.S. Cl. ................................................ 356/337; 356/349
(58) Field of Search ....................................... 356/335, 336, 356/337, 338, 340, 341, 342, 343, 349, 345, 351, 237; 250/574, 575

(56) References Cited

U.S. PATENT DOCUMENTS

| 4,541,719 | * | 9/1985 | Wyatt | 356/343 |
| 4,571,081 | * | 2/1986 | Ford, Jr. | 356/338 |
| 4,764,013 | * | 8/1988 | Johnston | 356/338 |
| 5,343,290 | | 8/1994 | Batchelder et al. | 356/349 |
| 5,486,919 | * | 1/1996 | Tsuji et al. | 356/349 |
| 5,502,561 | * | 3/1996 | Hutchins et al. | 356/336 |

* cited by examiner

Primary Examiner—Frank G. Font
Assistant Examiner—Sang H. Nguyen
(74) Attorney, Agent, or Firm—John P. Wooldridge; Alan H. Thompson

(57) ABSTRACT

A visible light method for detecting sub-100 nm size defects on mask blanks used for lithography. By using optical heterodyne techniques, detection of the scattered light can be significantly enhanced as compared to standard intensity detection methods. The invention is useful in the inspection of super-polished surfaces for isolated surface defects or particulate contamination and in the inspection of lithographic mask or reticle blanks for surface defects or bulk defects or for surface particulate contamination.

29 Claims, 3 Drawing Sheets

INSPECTION OF LITHOGRAPHIC MASK BLANKS FOR DEFECTS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to surface particle detection, and more specifically, it relates to the detection of defects on lithographic mask blanks.

2. Description of Related Art

The proposed 1999 SIA Technology Roadmap for Semiconductors is accelerating the reduction in dense line critical dimensions (CDs) to 23 nm by the year 2011. This will put a tremendous burden on mask fabrication, particularly in the area of defect detection and reduction. Mask defects as small as one-eighth the equivalent CD are printable and may cause chip failure. Table 1 shows the maximum permissible defect size for each lithography generation out to the year 2011.

TABLE 1

| Year of first shipment | 1999 | 2002 | 2005 | 2008 | 2011 | 2014 |
|---|---|---|---|---|---|---|
| Generation (nm) | 180 | 130 | 100 | 70 | 50 | 35 |
| Maximum mask defect size (nm) | 90 | 65 | 50 | 35 | 25 | 18 |

(assuming a lithography tool magnification of 0.25)

A new infrastructure for mask inspection will be required to keep pace with this aggressive roadmap. Depending on the specific lithography used for a particular generation, mask inspection specifics may change, but the methodology will essentially remain the same. Mask blanks will have to undergo 100% area inspection for defects larger than a maximum acceptable size. Since masks are becoming a significant cost factor in the cost of ownership of lithography tools, this is a critical step—patterning defective mask blanks would be an economic disaster.

Inspecting mask blanks can be approached differently than patterned masks. Inspection does not necessarily have to be done at-wavelength since defects at the mask blank level will interact with visible light. Techniques using visible light are appealing because they are familiar to the user, relatively straightforward to manufacture and, if designed properly, extendable over many generations.

Current wafer inspection tools could play this role if silicon wafers are used as the mask blanks, but this is unlikely due to unfavorable thermal properties. Even then, detection of defects smaller than 100 nm has not been demonstrated with these tools. Wafer inspection tools operate by measuring the intensity of the light scattered by a surface defect. FIG. 1 shows a typical optical system used for commercial wafer inspection. However, scatter decreases as the sixth power of the defect size, so as the critical defect size decreases, defects become extremely difficult to detect, i.e., as the defect size decreases, the scatter decreases by the fractional decrease in defect size to the $6^{th}$ power. Additionally, this scattered intensity inspection technique cannot distinguish surface defects from internal defects in transparent substrates such as ULE, a prime candidate for future mask blanks. As shown in FIG. 1, incident light beam 10 having S and P polarizations, is directed onto a mask blank 12 at the site of a defect 14. Scattered light 16, scattered from defect 14 is collected with collector mirrors 18 and 19 and directed to detector 20. This technique cannot distinguish whether the defect is located on the surface or within the transparent substrate.

SUMMARY OF THE INVENTION

It is an object of the present invention to provide new techniques for detecting a surface particle on a lithographic mask blank.

Defect detection, based on optical scattering, is a viable approach when there is sufficient signal-to-noise. Given a fixed amount of energy for illuminating the surface of the mask blank, typical instruments direct all of this light onto a given location on the mask blank and collect as much scattered light as possible (FIG. 1). If the fractional amplitude of the scattered light in a particular direction is 1/s, the intensity is proportional to $1/s^2$. Since the detected intensity falls off as the sixth power of the defect size, defects much smaller than the wavelength scatter very little light. For example, a 10 nm defect illuminated with a 1 mw beam focussed to a 10 um spot will scatter only $10^{-12}$ mw into a 0.1 numerical aperture.

The detected signal can be significantly amplified by making the following modifications:

(a) use part of the energy to illuminate the mask blank to scatter from a defect and use the remaining energy as a probe beam to coherently interfere with the scattered light (FIG. 5);

(b) frequency shift the probe beam (~10–1000 MHz) so that heterodyne detection can be used (FIG. 6); and (c) the incident angle and polarization of the illumination and probe beams are chosen to maximize the particle scatter and to minimize the noise from the background scatter in the direction of the specularly reflected probe beam.

DETAILED DESCRIPTION OF THE INVENTION

Figure 1:
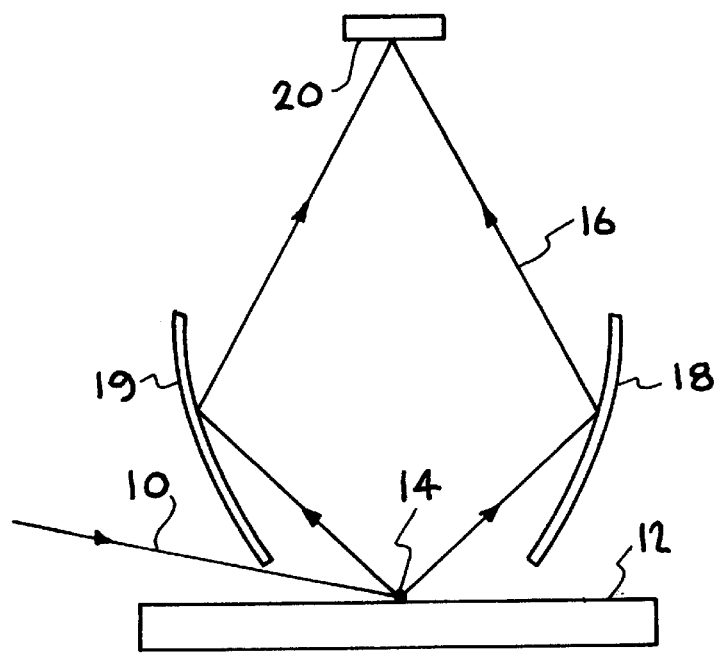
FIG. 1 shows an optical system used in commercial wafer inspection tools, based on measurement of scattered intensity.

In the present invention, the detected scattered light signal from a particle on a lithographic mask blank can be significantly amplified by (i) using a portion of the laser energy to illuminate the mask blank to scatter from a defect and using another portion of the laser energy as a probe beam to coherently interfere with the scattered light, (ii) frequency shifting the probe beam (~10–1000 MHz) so that heterodyne detection can be used; and (iii) choosing the incident angle and polarization of the illumination and probe beams to maximize the particle scatter and to minimize the noise from the background scatter in the direction of the specularly reflected probe beam.

Accordingly, the detected signal is proportional to the amplitude, 1/s, of the scattered light, a factor of s higher than conventional configurations. Using the same numerical values as above, the detected signal is now six orders of magnitude greater.

Equally important is the noise rejection of the proposed method. In conventional instruments, the signal-to-noise for small defects is limited by the constant background scatter from the inherent surface roughness of the mask blank and ambient light scattered from optics and air within the instrument. In the proposed method, heterodyne detection eliminates the contribution of all scattered light from outside the coherent probe volume, thereby minimizing background noise. This permits the surface inspection of transparent substrates that produce back surface and bulk scatter, such as ULE glass.

The exact geometry of the illumination and probe beams is chosen to maximize the signal-to-noise. The angle of incidence and polarization of the illumination beam and the angle and polarization of detection of the scattered light is chosen to maximize the detected scattered light from the particle and to minimize the detected scattered light from the substrate due to surface roughness. These angles are chosen based on electromagnetic simulations for particles of the size and refractive index that are expected on the surface of the substrate. The incident angle and polarization of the probe is then chosen so that the specularly reflected beam matches the angle and polarization of the detected scattered light.

In general the angular distribution of scattered light from a particle resting on a surface depends on the particle size, shape, and refractive index, and on the illumination beam incidence angle, wavelength and polarization. To model this angular distribution, particle size, shape and refractive index are defined by the specific application and the wavelength is chosen from a list of commercially available lasers. Angular distributions of the scattered light are then calculated for various angles of incidence and both S and P polarizations. These angular distributions show where the detector should be placed for maximum signal.

Likewise, the similar calculations are performed under the same conditions for light reflected from the non-ideal substrate that supports the particle. Microscopic surface imperfections (commonly called roughness), present on all surfaces, produce an angular distribution of scattered light. These angular distributions show where the detector should be placed for minimum noise.

In general the two detector positions do not coincide. However, the signal-to-noise can be optimized by taking the ratio of the two angular distributions to determine the optimal angular position to place the detector.

This method can be extended from defect detection to defect identification by the use of multiple probe beams. Since the angular distribution of scattered light is a signature of the particle, being a function of particle size, shape and refractive index, measurement of the angular distributions can be used to determine characteristics of the particle. The angular distribution is measured at different angular locations by using multiple probe beams, with slightly different frequencies to prevent electronic crosstalk.

The angular distributions showing the detector placements for maximum signal and minimum noise are calculated. Electromagnetic simulation codes are used to perform these calculations. The exact geometry of the illumination and probe beams will be chosen after careful modeling of the scatter from particles of different size and refractive index and from inherent surface roughness. These electromagnetic simulation codes are known in the art. One such code is known as TSAR (developed at Lawrence Livermore National Laboratory). A description of TSAR is found in "Using the TSAR electromagnetic modeling system" UCRL-ID 115227, September 1993, incorporated herein by reference and published by the University of California at Lawrence Livermore National Laboratory. Other commercially available codes include EMFLEX (Weidlinger Associates), Maxwell EMINENCE (Ansoft Corp.), MAFIA (CST) and DDSURF (ASU). A description of DDSURF is shown in a document titled "DDSURF/RDSURF User's Manual" ©1998 Arizona State University, incorporated herein by reference. The referenced document was authored by Brent M. Nedeker and E. Dan Hirleman, both of the Laser Diagnostics Laboratory, Arizona State University.

The computer codes, such as TSAR, that calculate the electromagnetic field scattered by a particle resting on a surface (e.g., a flat surface) and illuminated by an incident electromagnetic field are based on the coupled dipole approximation method. The dipoles are placed in a lattice configuration that models the physical geometry and material properties of the scattering particle. The response of each dipole is related to the incident electromagnetic field so that the dipole moment distribution can be calculated within the scattering particle. Knowing this distribution, the external scattered field can then be calculated in any direction from the scattering particle. To perform this calculation, a particle size, shape and refractive index are specified; the incident electromagnetic wavelength, polarization and incident angle are specified; and the refractive index of the flat substrate is specified.

Figure 2:
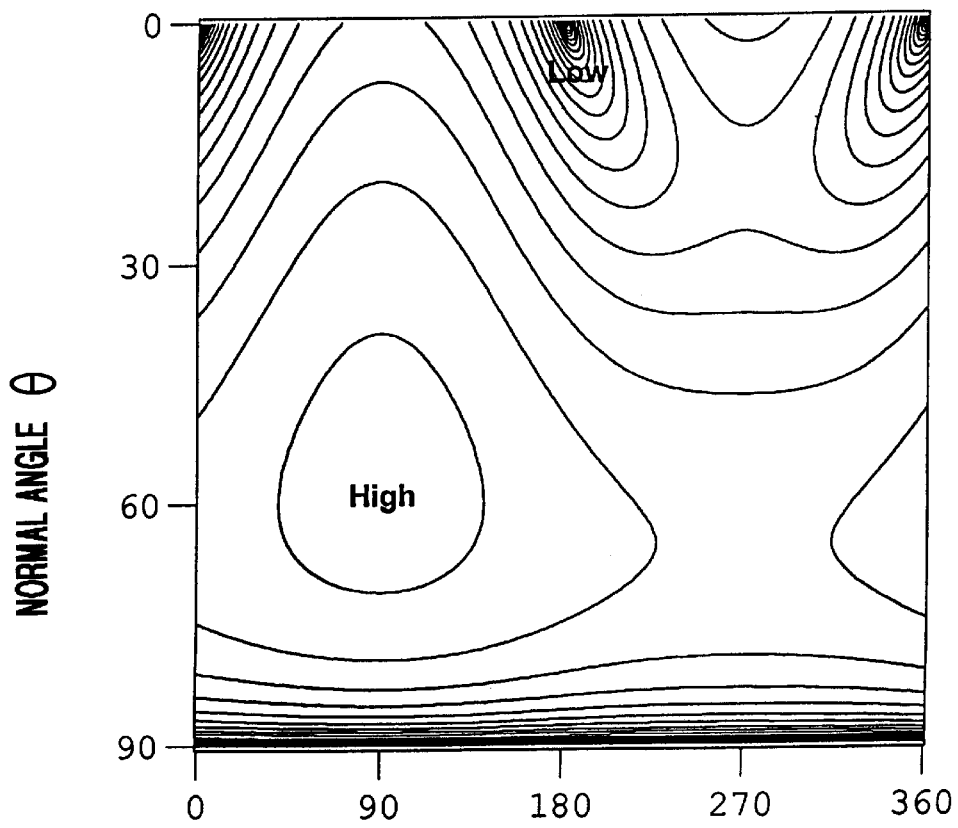
FIG. 2 shows the log angular scatter distribution from a 100 nm molybdenum particle.
Figure 3:
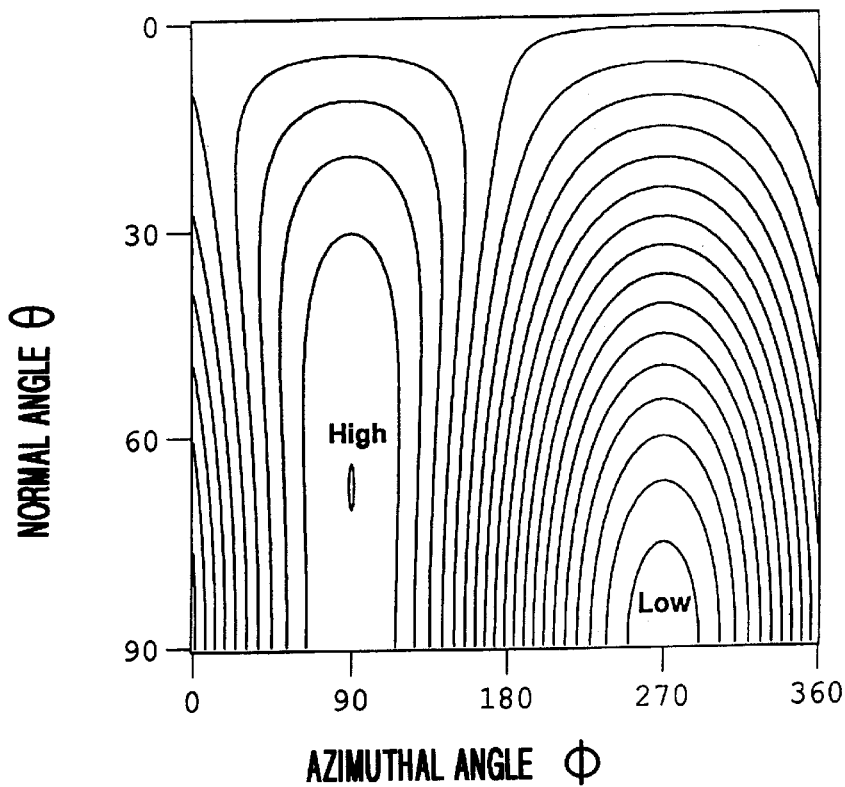
FIG. 3 shows the log angular scatter distribution from a 0.5 nm rms rough glass substrate
Figure 4:
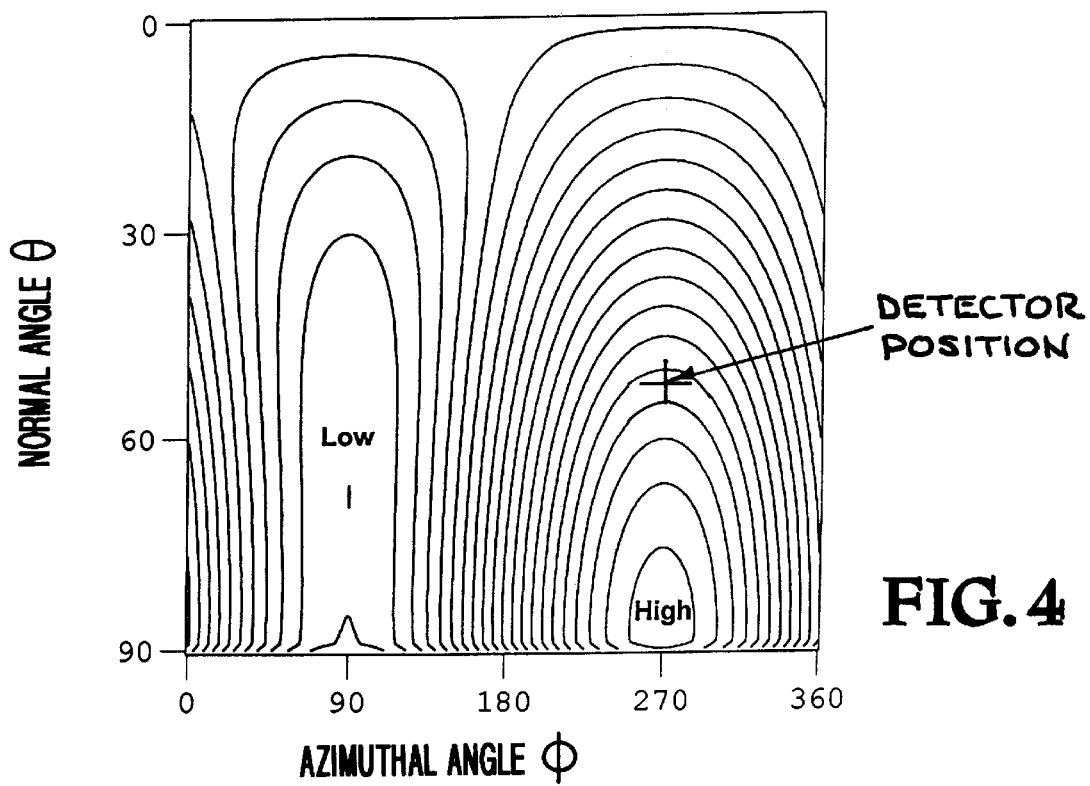
FIG. 4 shows the log signal-to-noise and the detector position.

FIG. 2 shows the log angular scatter distribution from a 100 nm molybdenum particle. FIG. 3 shows the log angular scatter distribution from a 0.5 nm rms rough glass substrate. FIG. 4 shows the log signal-to-noise and the detector position.

Figure 5:
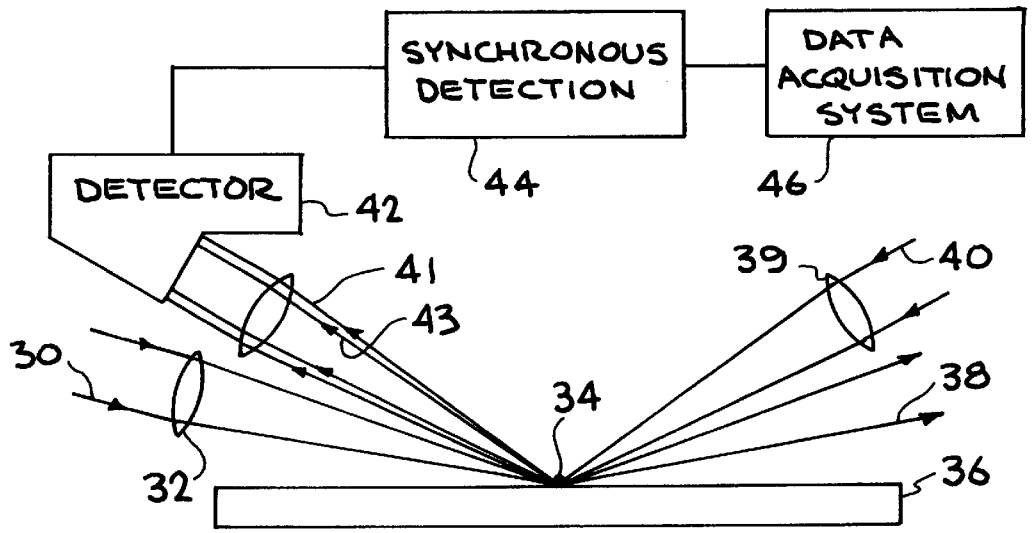
FIG. 5 shows an embodiment of the present invention that uses a probe beam to enhance scattered light from defects.

FIG. 5 shows an embodiment of the present invention. A laser produces a beam which is split into an incident beam and a probe beam. The incident beam and the probe beam are each passed through a separate Bragg cell which is configured to produce a frequency difference between the incident and probe beam. As shown in the figure, incident beam 30, comprising S and/or P polarized light, is focused by lens 32 onto mask blank 36 (comprising, e.g., ULE). Specularly reflected light 38 propagates out of the system. Defect 34, if present on mask blank 36, produces scattered light which is maximized at certain location(s). Mask blank 36 produces scattered light (background noise) which is minimized at certain locations. An electromagnetic simulation code is used to determine the position of maximum defect scatter and minimum background noise. Detector 42 is placed at the location of optimum signal-to-noise. Probe beam 40, comprising S and/or P polarized light, is focused by lens 39 onto mask blank 36 at the same location as beam 30. The angle of incidence is chosen so that the specularly reflected beam 41 is incident on detector 42, interfering with scattered light 43 from defect 34. The signal from detector 42 is sent through a synchronous detection module 44 and is then sent to a data acquisition system 46.

Figure 6:
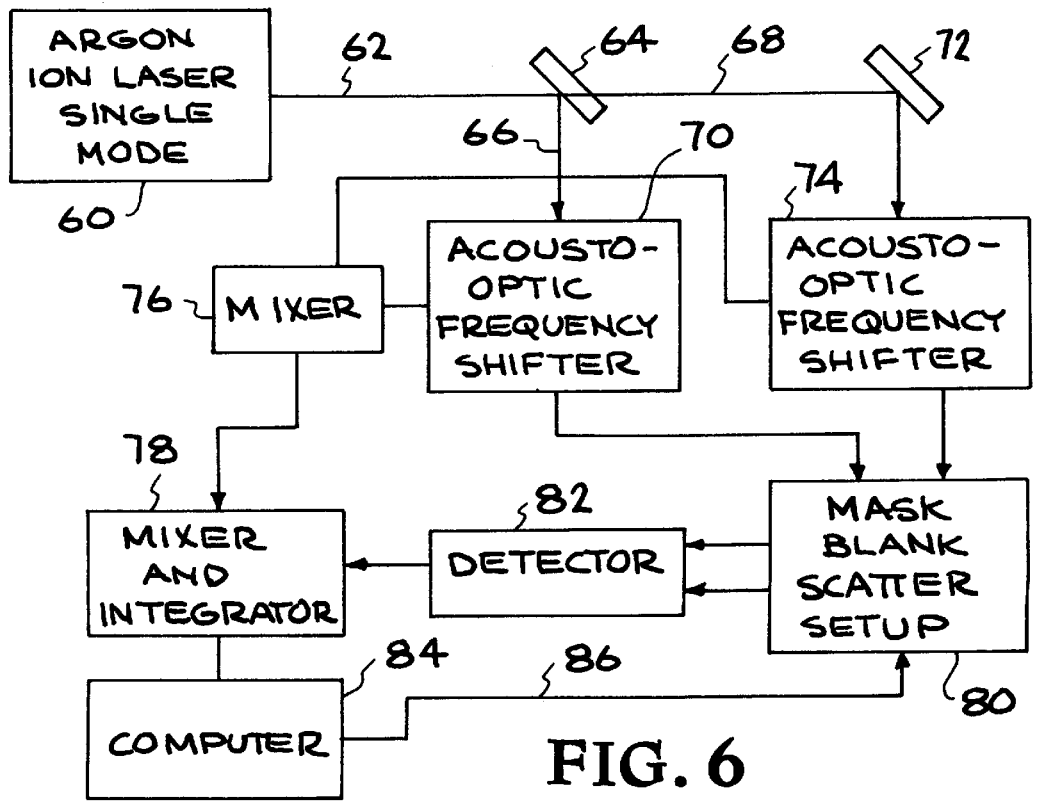
FIG. 6 shows a block type diagram that uses heterodyne detection to detect the presence of scattered light.

Another embodiment of the invention is shown in FIG. 6. In this embodiment, light beam 62 from a single laser 60 (e.g., an argon ion laser) is split into two beams by beamsplitter 64. The portion of light beam 62 that reflects from beamsplitter 64 is beam 66. The portion of light beam 62 that is transmitted through beamsplitter 64 is beam 68. Beam 66 passes through acousto-optic (AO) frequency shifter 70, which shifts the frequency of beam 66. In the embodiment shown, AO frequency shifter 70 shifts the frequency of beam 66 by 61 MHz. Beam 68 reflects from mirror 72 and passes through acousto-optic (AO) frequency shifter 74, which shifts the frequency of beam 68. In the embodiment shown, AO frequency shifter 74 shifts the frequency of beam 68 by 81 MHz. Thus, a 20 MHz frequency difference is generated between beam 66 and beam 68 to enable heterodyne detection. One of these two frequency shifted beams is used as the incident beam and the other beam is used as the probe beam.

A reference signal from each AO frequency shifter is sent to a mixer 76 the output of which is sent to a mixer/integrator 78. In a manner similar to the embodiment shown in FIG. 5, one of the output beams from the AO frequency shifter is used as an incident beam onto a defect or particle on mask blank 80 and the other output beam from the other AO frequency shifter is used as a probe beam onto mask blank 80. Detector 82 is placed at the location of maximum signal-to-noise and the output from detector 82 is integrated in mixer/integrator 78. The mixer/integrator output 78 is sent to a computer 84 for data acquisition. The embodiment may include input 86 from a computer (e.g., computer 78) to scanning stages connected to mask blank 80, as are known in the art.

To enhance detection performance, the incident angle and polarization are chosen to maximize the particle scatter and to minimize the noise from the background scatter.

To further enhance detection performance, the invention exploits the angular and polarization dependence of the scattered fields. Scattering from a defect will generally have a unique polarization and angular distribution signature depending on the defect geometry and refractive index. To take advantage of this fact, the surface is illuminated with both s and p polarizations and the corresponding scattered components are measured with multiple probe beams. These measurements allow us to better identify the specific defect.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A method for enhancing a detected signal from light scattered from a particle on an object, comprising:

determining an approximate first angular distribution of particle scatter signal produced by a first portion of a laser beam scattered from a particle, wherein said laser beam has an angle of incidence with respect to said object;

determining an approximate second angular distribution of object scatter noise produced by said first portion of said laser beam scattered from said object;

calculating a ratio of said approximate first angular distribution to said approximate second angular distribution to produce an approximate third angular distribution of particle scatter signal to object scatter noise;

placing a detector at a position chosen from said approximate third angular distribution;

directing said first portion of said laser beam at said angle of incidence to said particle to produce scattered light;

frequency shifting at a frequency difference a second portion of said laser beam with respect to said first portion of said laser beam to produce a frequency shifted laser beam;

directing said frequency shifted laser beam at said object to produce specularly reflected light directed at said detector; and detecting optical heterodyning, at said frequency difference, between a portion of said scattered light and a portion of said specularly reflected light to produce enhanced scattered light signal from said detector.

2. The method of claim 1, wherein said object comprises a lithographic mask blank.

3. The method of claim 1, wherein said particle has a size within a range of 18 nm to 180 nm.

4. The method of claim 1, wherein the step of determining an approximate first angular distribution comprises utilizing a library.

5. The method of claim 4, wherein said library comprises a database.

6. The method of claim 1, wherein the step of determining the approximate first angular distribution comprises calculating said first angular distribution.

7. The method of claim 6, wherein the step of calculating said first angular distribution comprises:

modeling the physical geometry and material properties of said particle by placing dipoles representing said particle in a lattice configuration;

calculating the dipole moment distribution within said particle to determine the response of each said dipole to said first portion of said laser beam; and calculating said first angular distribution from said dipole moment distribution.

8. The method of claim 6, wherein the step of calculating said first angular distribution comprises utilizing an electromagnetic simulation code.

9. The method of claim 8, wherein said electromagnetic simulation code comprises the TSAR code.

10. The method of claim 8, wherein said electromagnetic simulation code comprises the DDSURF code.

11. The method of claim 8, wherein said electromagnetic simulation code comprises a code selected from a group consisting of TSAR, EMFLEX, EMINENCE, MAFIA and DDSURF.

12. The method of claim 1, wherein the step of determining an approximate second angular distribution comprises utilizing a library.

13. The method of claim 12, wherein said library comprises a database.

14. The method of claim 1, wherein the step of determining the approximate second angular distribution comprises calculating said second angular distribution.

15. The method of claim 14, wherein the step of calculating said second angular distribution comprises:

modeling the physical geometry and material properties of said particle by placing dipoles representing said particle in a lattice configuration;

calculating the dipole moment distribution within said particle to determine the response of each said dipole to said first portion of said laser beam; and calculating said second angular distribution from said dipole moment distribution.

16. The method of claim 14, wherein the step of calculating said second angular distribution comprises utilizing an electromagnetic simulation code.

17. The method of claim 16, wherein said electromagnetic simulation code comprises the TSAR code.

18. The method of claim 16, wherein said electromagnetic simulation code comprises the DDSURF code.

19. The method of claim 16, wherein said electromagnetic simulation code comprises a code selected from a group consisting of TSAR, EMFLEX, EMINENCE, MAFIA and DDSURF.

20. The method of claim 1, wherein said position chosen from said approximate third angular distribution comprises a position of optimal particle scatter signal to object scatter noise.

21. The method of claim 1, wherein said position chosen from said approximate third angular distribution comprises a position of maximum particle scatter signal to object scatter noise.

22. The method of claim 1, wherein the step of frequency shifting is carried out with an acousto-optic frequency shifter.

23. The method of claim 1, wherein said frequency difference is within a range of 10 MHz to 1000 MHz.

24. The method of claim 1, wherein said angle of incidence of said first portion of said laser beam comprises a plurality of angles of incidence.

25. The method of claim 1, wherein said first portion of said laser beam comprises S polarization.

26. The method of claim 1, wherein said first portion of said laser beam comprises P polarization.

27. A method for enhancing a detected signal from light scattered from a particle on an object, comprising:

calculating an approximate first angular distribution of particle scatter signal produced by a first portion of a laser beam scattered from a particle, wherein said laser beam has an angle of incidence with respect to said object;

calculating an approximate second angular distribution of object scatter noise produced by said first portion of said laser beam scattered from said object;

calculating a ratio of said approximate first angular distribution to said approximate second angular distribution to produce an approximate third angular distribution of particle scatter signal to object scatter noise;

placing a detector at a position chosen from said approximate third angular distribution;

directing said first portion of said laser beam at said angle of incidence to said particle to produce scattered light;

frequency shifting at a frequency difference a second portion of said laser beam with respect to said first portion of said laser beam to produce a frequency shifted laser beam;

directing said frequency shifted laser beam at said object to produce specularly reflected light directed at said detector; and detecting optical heterodyning, at said frequency difference, between a portion of said scattered light and a portion of said specularly reflected light to produce enhanced scattered light signal from said detector.

28. A method for enhancing a detected signal from light scattered from a particle on an object, comprising:

determining a first angular distribution of particle scatter signal produced by a first portion of a laser beam scattered from a particle, wherein said laser beam has an angle of incidence with respect to said object;

determining a second angular distribution of object scatter noise produced by said first portion of said laser beam scattered from said object;

calculating a ratio of said first angular distribution to said second angular distribution to produce a third angular distribution of particle scatter signal to object scatter noise;

placing a detector at a position chosen from said approximate third angular distribution;

directing said first portion of said laser beam at said angle of incidence to said particle to produce scattered light;

frequency shifting at a frequency difference a second portion of said laser beam with respect to said first portion of said laser beam to produce a frequency shifted laser beam;

directing said frequency shifted laser beam at said object to produce specularly reflected light directed at said detector; and detecting optical heterodyning, at said frequency difference, between a portion of said scattered light and a portion of said specularly reflected light to produce enhanced scattered light signal from said detector.

29. An apparatus for enhancing a detected signal from light scattered from a particle on an object, comprising:

means for calculating an approximate first angular distribution of particle scatter signal produced by a first portion of a laser beam scattered from a particle, wherein said laser beam has an angle of incidence with respect to said object;

means for calculating an approximate second angular distribution of object scatter noise produced by said first portion of said laser beam scattered from said object;

means for calculating a ratio of said approximate first angular distribution to said approximate second angular distribution to produce an approximate third angular distribution of particle scatter signal to object scatter noise;

a detector placed at a position chosen from said approximate third angular distribution;

means for directing said first portion of said laser beam at said angle of incidence to said particle to produce scattered light;

means for frequency shifting at a frequency difference a second portion of said laser beam with respect to said first portion of said laser beam to produce a frequency shifted laser beam; and means for directing said frequency shifted laser beam at said object to produce specularly reflected light directed at said detector, wherein said detector detects optical heterodyning, at said frequency difference, between a portion of said scattered light and a portion of said specularly reflected light to produce enhanced scattered light signal from said detector.

* * * * *